United States Patent [19]

Osugi et al.

[11] Patent Number: 4,666,945

[45] Date of Patent: May 19, 1987

[54] CATALYST COMPOSITION SUITABLE FOR SYNTHESIS OF METHANOL

[75] Inventors: Minoru Osugi; Makoto Takagawa; Tadasi Nakamura; Takashi Kojima; Kinya Tsuji, all of Niigata, Japan

[73] Assignee: Mitsubishi Gas Chemical Company, Inc., Tokyo, Japan

[21] Appl. No.: 775,114

[22] Filed: Sep. 11, 1985

Related U.S. Application Data

[62] Division of Ser. No. 669,460, Nov. 8, 1984.

[30] Foreign Application Priority Data

Nov. 14, 1983 [JP] Japan ................... 58-213839

[51] Int. Cl.⁴ ............... C07C 27/06; C07C 27/08
[52] U.S. Cl. .................... 518/713; 518/713; 502/208; 502/307; 502/342; 502/343
[58] Field of Search ....................... 518/713

[56] References Cited

U.S. PATENT DOCUMENTS

| | | | |
|---|---|---|---|
| 2,061,470 | 1/1936 | Larson | 518/713 |
| 3,961,037 | 6/1976 | Davies et al. | 502/342 X |
| 4,111,847 | 9/1978 | Stiles | 518/713 |
| 4,149,009 | 4/1979 | Yoneoka et al. | 502/343 X |
| 4,279,781 | 7/1981 | Dienes et al. | 518/713 |
| 4,483,943 | 11/1984 | Windawi et al. | 518/713 |
| 4,507,403 | 3/1985 | Asakawa | 518/713 |

OTHER PUBLICATIONS

Consedine et al, Van Nostrands Scientific Encyclopedia, Sixth Ed., Van Nostrand Reinhold Company, New York, 1983, p. 543.

Primary Examiner—Howard T. Mars
Attorney, Agent, or Firm—Wenderoth, Lind & Ponack

[57] ABSTRACT

A catalyst composition comprising copper oxide, zinc oxide and zirconium oxide, the content of zirconium oxide being 30 to 70% by weight. This catalyst composition is useful for synthesis of methanol from carbon monoxide and/or carbon dioxide and hydrogen by a gas-liquid-solid phase fluidized bed method or a gas-solid phase fluidized bed method.

4 Claims, No Drawings

CATALYST COMPOSITION SUITABLE FOR SYNTHESIS OF METHANOL

This application is a division of now abandoned application Ser. No. 669,460, filed Nov. 8, 1984.

This invention relates to a novel catalyst composition suitable for synthesis of methanol, and more specifically to a catalyst composition having excellent abrasion resistance and catalytic activity which is suited for use in a fluidized catalyst bed when producing methanol from carbon monoxide and/or carbon dioxide and hydrogen by a vapor-phase method.

Synthesis of methanol from carbon monoxide and/or carbon dioxide and hydrogen is commonly performed in the presence of a fixed bed catalyst. The methanol synthesis reaction is a considerable heat generation reaction, and varying methods for removal of a heat of reaction occurring in a reactor have been hitherto proposed. However, in recent years, change in raw materials for chemical industry has led one to find sources of raw materials in heavy oils, coals and surplus gases generated in iron mills. Contents of carbon monoxide and carbon dioxide in starting gases obtained from these surplus gases are relatively higher than a content of hydrogen. Accordingly, when said starting gases are used in synthesis of methanol, a temperature distribution in a reactor tends to get non-uniform, and a conventional reactor of a fixed bed catalyst system cannot adapt enough to the use of starting gases. Moreover, a method of circulating large amounts of unreacted gases which has been generally employed in the ordinary fixed bed catalyst system has increased expenses for power, and especially a recent tendency for apparatuses to be scaled up has made the problem more serious.

In order to resolve such problem, a method is considered wherein methanol is synthesized in a fluidized bed. In this instance, however, catalyst particles are worn away and smashed because the catalyst particles impinge against one another or against the wall of the reactor. If the conventional catalysts for synthesis of methanol in a fixed bed are utilized as such in a fluidized bed, necessary abrasion resistance is not obtainable, and this has interfered with realization of a method for synthesizing methanol in a fluidized bed.

The present inventors have made extensive studies to develop catalysts showing high activity for synthesis of methanol and such abrasion resistance as to fully withstand the practical use in a gas-liquid-solid three-phase fluidized bed method wherein methanol is synthesized by feeding starting gases to a solid dispersed liquid phase with a catalyst dispersed in an inert medium such as hydrocarbon oils, etc. as well as in the usual gas-phase fluidized bed method. In consequence, they have discovered that the above purpose can be achieved by containing in a catalyst a large amount of zirconium oxide and if necessary, an aluminum compound, a chromium compound, a magnesium compound, a vanadium compound or a phosphorus compound.

Thus, the present invention is to provide a three-component catalyst composition comprising copper oxide, zinc oxide and zirconium oxide, the content of zirconium oxide being 30 to 70% by weight.

Moreover, the present invention is to provide a four-component catalyst composition obtained by further adding 1 to 50% by weight, based on the total amount of copper oxide and zinc oxide, of a compound selected from chromium oxide, vanadium oxide, magnesium oxide, aluminum oxide and an oxyacid of phosphorus or its salt to a catalyst composition comprising copper oxide, zinc oxide and zirconium oxide, the content of zirconium oxide being 30 to 70% by weight.

Catalysts for synthesis of methanol in a fixed bed, containing copper oxide, zinc oxide and zirconium oxide, are described in e.g. British Patent No. 1436773 and Japanese Laid-open Patent Application No. 67352/83. However, these applications simply teach that zirconium may be added as a stabilizer or carrier, failing to disclose concrete Examples. The above known literature is therefore devoid of a confirmation of effects about in what composition range the catalysts have necessary abrasion resistance as fluidized bed catalysts. Not only that, but also their activity is low, and said catalysts are unsatisfactory. Particularly, no mention is made of a four-component catalyst comprising copper oxide, zinc oxide, zirconium oxide, and a compound selected from chromium oxide, vanadium oxide, magnesium oxide and an oxyacid of phosphorus or its salt.

The catalyst composition of this invention may consist essentially of an intimate mixture of three essential components, copper oxide, zinc oxide and zirconium oxide. The catalyst of this invention features that zirconium oxide is used as a component to impart abrasion resistance necessary as a fluidized bed catalyst to the catalyst. It has been found this time that in order to exhibit such abrasion resistance, it is very important that the content of zirconium oxide is within the range of 30 to 70% by weight based on the weight of the catalyst composition. When the content of zirconium oxide is less than 30% by weight, the resulting catalyst composition cannot have satisfactory abrasion resistance. Meanwhile, when said content exceeds 70% by weight, activity of the resulting catalyst composition is low and a space time yield of methanol decreases, which is industrially disadvantageous. Thus, a preferable content of zirconium oxide is 30 to 70% by weight, more preferably 40 to 60% by weight based on the weight of the catalyst composition.

On the other hand, contents of copper oxide and zinc oxide vary with the content of zirconium oxide, etc. In general, the content of copper oxide is 10 to 67% by weight, preferably 18 to 56% by weight, more preferably 18 to 50% by weight. The content of zinc oxide is 3 to 20% by weight, preferably 4 to 22% by weight, more preferably 10 to 22% by weight. A ratio of copper oxide to zinc oxide in the catalyst composition is not strictly limited and can be changed depending on conditions for a methanol synthesis reaction using said catalyst composition. It is usually profitable that copper oxide and zinc oxide are present in such proportions that a Cu/Zn atomic ratio is 0.5/1 to 20.0/1, preferably 0.8/1 to 15.0/1, more preferably 0.8/1 to 5/1.

Moreover, the catalyst composition of this invention can provide a catalyst having a better activity by containing, in addition to the aforesaid three essential components, copper oxide, zinc oxide and zirconium oxide, a compound selected from chromium oxide, vanadium oxide, magnesium oxide, aluminum oxide and an oxyacid of phosphorus or its salt. Most preferable of these compounds are the phosphorus and aluminum compounds. Amounts of these additional catalyst components vary with their types, conditions used for methanol synthesis reaction. Generally speaking, it is suitable that they are present in amounts of 1 to 50% by weight, preferably 1 to 25% by weight, more preferably 1 to 10% by weight based on the total weight of copper oxide and zinc oxide. Advantageously, the above additional catalyst components are contained in such proportions that an atomic ratio of said metals or phosphorus to zinc to 0.001:1 to 10:1, preferably 0.005:1 to 5:1, more preferably 0.005:1 to 1:1.

The three-component catalyst of this invention can be prepared by, for example, forming into fine particles uniform mixture of water-insoluble copper-, zinc- and zirconium compounds convertible to copper-, zinc- and zirconium oxides respectively under the calcination conditions to be later described, and then subjecting the fine particles to calcination treatment.

The uniform mixture of the water-insoluble copper-, zinc- and zirconium compounds can be prepared by, for example, varied methods to be described below.

(a) A method which comprises adding a suitable precipitating agent to a mixed aqueous solution of water-soluble copper-, zinc- and zirconium compounds to coprecipitate a mixture of water-insoluble copper-, zinc- and zirconium compounds.

(b) A method wherein from a mixed aqueous solution of the two of a water-soluble copper compound, a water-soluble zinc compound and a water-soluble zirconium compound, two water-insoluble metal compounds are coprecipitated, the remaining water-soluble metal compound is added and dissolved, and its water-insoluble metal compound is then precipitated; or the slurry of the remaining water-insoluble metal compound separately precipitated is added to the above coprecipitated slurry; or the above procedure is conducted in reverse order.

(c) A method which comprises precipitating a water-insoluble copper compound, a water-insoluble zinc compound and a water-insoluble zirconium compound separately from an aqueous solution of a water-soluble copper compound, an aqueous solution of a water-soluble zinc compound and an aqueous solution of a water-soluble zirconium compound, then mixing them in the form of a precipitated slurry, or separating the respective precipitates by filtration and then kneading them with one another.

(d) A method wherein in order to form a mixed aqueous slurry of a water-insoluble copper and/or zirconium compound and a water-insoluble zinc compound in the above method (b), zinc oxide or zinc hydroxide is added to a water-insoluble copper and/or zirconium compound precipitated from an aqueous solution of a water-soluble copper and/or zirconium compound to form an aqueous slurry, and then blowing a carbon dioxide gas into the aqueous slurry to convert zinc oxide or zinc hydroxide to a basic zinc carbonate.

Water-soluble copper compounds used as starting materials in these methods include water-soluble copper salts usually employed for the preparation of the aforesaid conventional catalysts. Specific examples are cupric nitrate, cupric acetate and cupric oxalate. Those which do not contain elements acting as catalyst poisons such as halogen and sulfur are preferred. Cupric nitrate is especially preferred.

Water-soluble zinc compounds may be any water-soluble zinc salts which are usually employed for the preparation of the aforesaid conventional catalysts. Specific examples include zinc nitrate and zinc acetate. Of these salts, preferred are those not containing elements that become catalyst poisons such as halogen and sulfur. Zinc nitrate is particularly preferred.

Examples of the water-soluble zirconium compound available in the above methods include organic or inorganic acid salts of zirconium such as zirconium oxynitrate and zirconium acetate. It is also advisable that these salts do not either contain elements that become catalyst poisons, such as halogen and sulfur. Zirconium oxynitrate is especially preferred.

In order to form a water-insoluble zirconium compound, it is also possible to use zirconium compounds soluble in a suitable solvent and forming a precipitate under suitable conditions, for example, zirconium alkoxides such as zirconium tetrabutoxide. The zirconium alkoxide can dissolve in a solvent such as an alcohol and upon addition of water, form a water-isoluble zirconium compound.

It should be thus understood in the above-described methods that in the formation of the water-insoluble zirconium compound, the solution of zirconium alkoxide can replace the aqueous solution of the water-soluble zirconium compound.

In the aforesaid methods, examples of the precipitating agent available in the (co)precipitation of the water-insoluble copper- and/or zinc- and/or zirconium compound(s) from the aqueous solution(s) of the water-soluble copper- and/or zinc- and/or zirconium compound(s) can be water-soluble alkaline substances such as ammonia; alkali carbonates such as sodium carbonate, potassium carbonate, lithium carbonate and ammonium carbonate; alkali bicarbonates such as sodium bicarbonate, potassium bicarbonate and ammonium bicarbonate; and alkali metal hydroxides such as sodium hydroxide, potassium hydroxide and lithium hydroxide. These precipitating agents can usually be employed in amounts of at least 0.8 equivalent, preferably 1 to 2 equivalents, more preferably 1.0 to 1.3 equivalents.

The reaction of forming the precipitate of the water-insoluble metal compound(s) from the aqueous solution(s) of the water-soluble metal compound(s) can be performed according to methods known per se, e.g. methods described in U.S. Pat. Nos. 3,971,735 and 4,305,842 as well as UK Patent Application No. 2064352A. The reaction may be carried out, for example, at room temperature or if required, on heating up to about 90° C. Under such conditions, the reaction can proceed smoothly and be terminated almost quantitatively within several minutes or several tens minutes.

The concentration each of the water-soluble metal compounds in the aqueous solution in the precipitation reaction is not critical and can vary broadly depending on types of the compounds. Generally, it is 0.05 mole/liter to the limit of dissolution of the compound(s), preferably 0.1 to 5 mole/liter.

The thus formed uniform mixture of the water-insoluble copper-, zinc- and zirconium compounds is filtered, washed if necessary and then formed into a slurry in a concentration suited for pulverization. The slurry solution is formed into fine particles by spray-drying or dropping it in oil in a usual manner.

The concentration of the slurry varies with the composition of the uniform mixture, pulverizing method, etc. Generally speaking, it is convenient that the concentration is set such that the solids content is 5 to 40% by weight, preferably 10 to 30% by weight based on the aqueous medium.

To prepare the four-component catalyst composition containing the additional catalyst component besides the three components, copper oxide, zinc oxide and zirconium oxide, it is also possible that in any optional stage during formation of the uniform mixture of water-insoluble copper, zinc, and zirconium compounds, the water-insoluble compound of the additional catalytically active metal is (co)precipitated from the aqueous solution containing the water soluble compound of the additional catalytically active metal, or a fine powder of chromic anhydride and alumina sol or other water-insoluble compound of said additional metal is added, or the above obtained uniform mixture is further mixed with an oxyacid of phosphorus or its salt (see U.K. Patent Application No. 101563A).

Examples of the additional metal compound include aluminum compounds such as aluminum nitrate, aluminum oxide, aluminum hydroxide, sodium aluminate and aluminum acetate, chromium compounds such as chromium hydroxide, chromium oxide, sodium chromate, chromium nitrate, chromic anhydride and potassium bichromate; vanadium compounds such as vanadium oxide, ammonium vanadate and vanadium oxynitrate; and magnesium compounds such as magnesium carbonate, magnesium hydroxide, magnesium oxide, magnesium nitrate, magnesium chromate and magnesium aluminate.

Examples of the oxyacid of phosphorus or its salt available as one additional catalyst component include orthophosphoric acid, pyrophosphoric acid, polyphosphoric acid, metaphosphoric acid, phosphorous acid, hypophosphorous acid and metal salts of these acids. There is no particular restriction on the metals forming the metal salts, but inclusion of oxygen-family elements (excepting oxygen) such as sulfur, halogen family elements, and alkali metals such as sodium and potassium should be avoided.

Specific examples of such metal salts are orthophosphates such as copper phosphate, silver phosphate, magnesium pholsphate, magnesium hydrogen phosphate, magnesium dihydrogen phosphate, calcium phosphate, calcium hydrogen phosphate, calcium dihydrogen phosphate, strontium phosphate, barium hydrogen phosphate, zinc phosphate, cadmium phosphate, aluminum phosphate, tin pholsphate, lead phosphate, lead hydrogen phosphate, titanyl phosphate, zirconyl phosphate, bismuth pholsphate, chromium phosphate, manganese phosphate, manganese hydrogen phosphate, ferrous phosphate, ferric phosphate, cobalt phosphate and nickel phosphate; pyrophosphates such as copper pyrophosphate, magnesium pyrophosphate, calcium pyrophosphate, zinc pyrophosphate and manganese pyrophosphate; polyphosphates such as calcium tripolyphosphate and magnesium tripolyphosphate; metaphosphates such as magnesium metaphosphate, calcium metaphosphate, barium metaphosphate and aluminum metaphosphate; phosphites such as magnesium phosphite, calcium phosphite, germanium phosphite and lead phosphite (dibasic); and hypophosphites such as magnesium hypophosphite, calcium hypophosphite, barium hypophosphite and manganese hypophosphite. Among these oxyacids of phosphorus and their salts, magnesium phosphate, calcium hydrogen phosphate, calcium phosphite, calcium phosphate, zirconyl phosphate, magnesium pyrophosphate, calcium pyrophosphate, magnesium tripolyphosphate and calcium metaphosphate are especially preferred for use in this invention.

The uniform mixture formed in fine particles as above is then calcined. The calcination can be carried out by a method known per se such that the mixture is heated at at least 280° C., preferably 300° to 500° C. for about 0.3 to 3 hours in an atmosphere of air, a combination gas, etc. and in a calcination furnace such as an electrical furnace or a gas calcination furnace.

The thus prepared powdery catalyst composition is able to have the same particle size of 5 to 3,000 microns as used in an ordinary fluidized catalyst bed reactor. When said composition is employed in a gas-phase fluidized catalyst bed reaction, a good fluidized condition cannot be at times obtained in case of particles with a particle size of more than 500 microns being present in large amounts. Generally preferred are almost spherical particles with a particle size of 20 to 400 microns having a suitable particle size distribution.

The catalyst composition of this invention, after it is subjected to an activation treatment such as reduction with hydrogen as is usually practiced, can be used as a fluidized bed catalyst for various reactions, for example, a reaction of synthesizing methanol from a gaseous mixture of carbon monoxide and/or carbon dioxide and hydrogen, a carbon monoxide conversion reaction, a hydrogenation reaction, and a methanol decomposition reaction.

The activation treatment of the catalyst composition of the invention may be carried out in a customary manner, for example, by reducing it with a hydrogen-containing gas. For example, it is carried out in a reducing atmosphere such as a starting gas for synthesis of methanol by raising the temperature of the catalyst composition gradually from about 140° C. to avoid abrupt generation of heat, and finally maintaining the catalyst composition at 240° C. for 3 hours.

The activated catalyst composition is particularly suitable for catalyzing synthesis of methanol using a fluidized catalyst bed from a gaseous mixture of carbon monoxide and/or carbon dioxide and hydrogen. Synthesis of methanol with the catalyst composition of this invention can be carried out by a method known per se. for example by the method described in U.S. Pat. No. 4,386,017. For example, the synthesis reaction can be performed by feeding the aforesaid gaseous mixture into a reaction zone having a fluidized catalyst bed at a pressure of 20 to 300 kg/cm$^2$.G, preferably 30 to 200 kg/cm$^2$.G, a temperature of 150° to 350° C., preferably 200° to 300° C., and a space velocity of 1,000 to 80,000 hr$^{-1}$. Especially, when the composition is used in a gas-phase fluidized bed method, a gas space velocity is also to be considered for well fluidizing the catalyst particles.

The catalyst composition provided by the present invention is high in catalytic activity to synthesis of methanol and excellent in abrasion resistance, and can be advantageously employed in both (a) a method of methanol synthesis using a gas-liquid-solid three-phase fluidized bed wherein methanol is synthesized by dispersing a solid catalyst in an inert liquid medium such as a hydrocarbon oil and introducing carbon monoxide and/or carbon dioxide and hydrogen gas in the dispersion, and (b) a method of methanol synthesis using a gas-phase fluidized bed wherein methanol is synthesized while fluidizing the solid catalyst powder upon blowing carbon monoxide and/or carbon dioxide and hydrogen gas into a bed packed with the solid catalyst powder.

The following Examples illustrate this invention in more detail.

EXAMPLE 1

Copper nitrate trihydrate (317.4 g), 294.5 g of zinc nitrate hexahydrate and 400.9 g of zirconium oxynitrate dihydrate were dissolved in 10 l of deionized water, and the solution was held at 60° C. Said solution was added with stirring to a solution of 631 g of ammonium bicarbonate in 30 l of deionized water, maintained at 60° C. to form an insoluble precipitate. After the precipitate solution was stirred at 60° C. for 1 hour, the temperature was elevated to 80° C. for 30 minutes, followed by further stirring for 30 minutes. Subsequently, the resulting product was allowed to cool and filtered. The filtrate was washed four times with 10 l of deionized water.

To the thus obtained precipitate was added 10.6 g of chromic anhydride, and the mixture was kneaded for 2 hours. Thereafter, 1250 g of deionized water was added to prepare a slurry (slurry concentration 16% by weight). The slurry was fed to a disc-type spray dryer and dried at a dry air inlet temperature of 220° C. to afford 290 g of a spherical powder. The powder was fluidized under a stream of air in a glass tube having an inner diameter of 40 mm and provided in a lower portion with a glass filter, and calcined at 380° C. for 1.5 hours to obtain 225 g of a catalyst A having properties shown in Table 1.

EXAMPLE 2

Zirconium oxyacetate (317.7 g) was dissolved in 5 l of deionized water and the solution was maintained at 40° C. Said solution was added with stirring to a solution of 164.4 g of sodium carbonate in 10 l of deionized water, maintained at 40° C. to form an insoluble precipitate. Subsequently, 20 l of a solution containing 341.3 g of sodium carbonate was added, and the mixture was heated to 60° C. for 30 minutes. Five liters of a solution containing 317.4 g of copper nitrate trihydrate, 294.5 g of zinc nitrate hexahydrate and 7.45 g of vanadium oxynitrate was added to the reaction mixture, and the temperature was then elevated to 80° C. for 30 minutes, followed by ageing for 30 minutes. After cooling, filtration and washing were carried out as in Example 1, and a slurry (slurry concentration 14% by weight) was formed by a kneader. Spray drying and calcining were conducted as in Example 1 to provide 210 g of a catalyst B having properties shown in Table 1.

EXAMPLE 3

Copper nitrate trihydrate (317.4 g), 294.5 g of zinc nitrate hexahydrate, 25.54 of magnesium nitrate trihydrate and 400.9 g of zirconium oxynitrate were dissolved in 10 l of deionized water and the solution was maintained at 60° C. Said solution was added with stirring to a solution of 648 g of ammonium bicarbonate in 30 l of deionized water, maintained at 60° C. to form an insoluble precipitate. Subsequently, the temperature was raised to 80° C. over the course of 20 minutes. The reaction mixture was aged for 30 minutes, and filtered. The filtrate was washed and kneaded with a kneader to form a slurry (slurry concentration 18% by weight).

In the same way as in Example 1, spray drying and calcining were conducted to obtain a catalyst C having properties shown in Table 1.

EXAMPLE 4

Ammonium bicarbonate (327.6 g) was dissolved in 10 l of deionized water and the solution was maintained at 40° C. A solution of 377.8 g of zirconium oxynitrate in 5 l of deionized water, maintained at 40° C., was added to the above solution with stirring to form a precipitate. To the mixture was then added a solution of 400 g of ammonium bicarbonate in 20 l of deionized water, and the resulting mixture was stirred for 30 minutes. Subsequently, a solution obtained by dissolving 317.4 g of copper nitrate trihydrate and 294.5 g of zinc nitrate in 5 l of deionized water was added and the mixture was heated to 80° C. over the course of 40 minutes and aged for 30 minutes. Filtering and washing were then conducted, and 3.6 g of calcium hydrogenphosphate and 1310 g of deionized water were added to the resulting cake, and the mixture was kneaded by a kneader to afford a slurry (slurry concentration 11% by weight). Spray drying and calcining were conducted as in Example 1 to obtain 202 g of a catalyst D having properties shown in Table 1.

EXAMPLE 5

Four hundred grams of ammonium bicarbonate was dissolved in 20 l of deionized water and the solution was maintained at 50° C. A solution obtained by dissolving 317.4 g of copper nitrate trihydrate and 294.5 g of zinc nitrate hexahydrate in 5 l of deionized water and maintained at 50° C., was added to the above solution with stirring to form a precipitate. The temperature was then elevated to 80° C. for 30 minutes. After ageing for 30 minutes, the resulting product was allowed to cool up to 55° C. Two liters of a solution containing 109 g of 10% alumina sol was added to this product, and the mixture was stirred for 10 minutes. Subsequently, 5 l of a solution of 377.8 g of zirconium oxynitrate dihydrate maintained at 40° C. and 10 l of a solution of 327.6 g of ammonium bicarbonate maintained at 40° C. were added to the above mixture simultaneously with stirring, followed by further stirring for 30 minutes. After the formed insoluble precipitate was filtered and the filtrate was washed, 1290 g of deionized water was added and the mixture was kneaded with a kneader to form a slurry (slurry concentration 17% by weight). In the same way as in Example 1, spray drying and calcining were performed to afford 230 g of a catalyst E having properties shown in Table 1.

EXAMPLE 6

The procedure in Example 5 was repeated except using 362.4 g of copper nitrate trihydrate, 337.2 g of zinc nitrate hexahydrate, 499.8 g of ammonium bicarbonate for forming a precipitate from these compounds, 278 g of zirconium oxynitrate dihydrate, 230.2 g of ammonium bicarbonate as a precipitating agent and 124.8 g of 10 wt. % alumina sol. There resulted 240 g of a catalyst F having properties shown in Table 1.

EXAMPLE 7

Ammonium bicarbonate (327.6 g) was dissolved in 10 l of deionized water and the solution was maintained at 40° C. A solution of 377.8 g of zirconium oxynitrate in 5 l of deionized water, maintained at 40° C., was added to the above solution with stirring to form a precipitate.

Meanwhile, 400 g of ammonium bicarbonate was dissolved in 20 l of deionized water and the solution was maintained at 40° C. Subsequently, a solution obtained by dissolving 317.4 g of copper nitrate trihydrate and 294.5 g of zinc nitrate hexahydrate in 5 l of deionized water and held at 40° C. was added to the above solution. The temperature was then elevated to 80° C. for 35 minutes, and the reaction mixture was aged for 30 minutes and allowed to cool up to 55° C. To the resulting cooled product was added 2 l of a solution containing 109 g of 10% alumina sol, and they were stirred for 30 minutes. This solution was mixed with the previously formed zirconium precipitate-containing solution under stirring. After vigorous stirring for 30 minutes, the mixture was filtered, and the filtrate was washed and kneaded with a kneader to form a slurry (slurry concentration 15% by weight). In the same way as in Example 1, spray drying and calcining were carried out to form a catalyst G having properties shown in Table 1.

EXAMPLE 8

The procedure in Example 7 was repeated except that alumina sol was not added. There resulted a catalyst H.

COMPARATIVE EXAMPLE 1

Eight hundred grams of ammonium bicarbonate was dissolved in 40 l of deionized water, and the solution was maintained at 50° C. A solution obtained by dissolving 634.8 g of copper nitrate trihydrate and 589 g of zinc nitrate hexahydrate in 10 l of deionized water and maintained at 50° C. was added to the above solution with stirring to form a precipitate. Subsequently, the temperature was elevated to 80° C. for 30 minutes. After the mixture was aged at this temperature for 30 minutes, it was allowed to cool up to 55° C. Four liters of an aqueous solution containing 218 g of 10 wt. % alumina sol was added to the cooled product, and the mixture was stirred for 10 minutes. After filtering and washing, 1405 g of deionized water was added to the resulting cake, and the mixture was kneaded with a kneader to form a slurry (slurry concentration 19% by weight). As in Example 1, spray drying and calcining were carried out to provide a catalyst I having properties shown in Table 1.

COMPARATIVE EXAMPLE 2

Seven liters of a solution containing 483.2 g of copper nitrate trihydrate and 446.0 g of zinc nitrate hexahydrate and maintained at 40° C. was mixed with 15.4 l of a solution containing 608.8 g of ammonium bicarbonate and maintained at 40° C. under stirring to form a precipitate. Subsequently, the temperature was elevated to 80° C. for 40 minutes, and the product was aged for 30 minutes. After cooling to 55° C., 2 l of a solution containing 275 g of 10% alumina sol was added to the aged product, and they were stirred for 15 minutes. Then, 2 l of a solution containing 267.3 g of zirconium oxynitrate dihydrate and maintained at 40° C. and 5.6 l of a solution containing 221.4 g of ammonium bicarbonate and maintained at 40° C. were added to the above mixture with stirring, followed by further continuing stirring for 30 minutes. The resulting insoluble precipitate was filtered and the filtrate was washed to form a slurry (slurry concentration 19% by weight). Thereafter, the slurry was spray dried and calcined as in Example 1 to afford a catalyst J having properties shown in Table 1.

COMPARATIVE EXAMPLE 3

Four liters of a solution containing 289.9 g of copper nitrate trihydrate and 269.0 g of zinc nitrate hexahydrate and held at 40° C. was mixed under stirring with 9 l of a solution containing 365.9 g of ammonium bicarbonate and held at 40° C. The precipitate was formed, then heated to 80° C. for 40 minutes and aged for 30 minutes. Thereafter, the aged product was cooled to ° C., and 1 l of a solution containing 91.8 g of 10 wt. % alumina sol was added to the cooled product, followed by stirring for 15 minutes. Subsequently, 8 l of a solution containing 1069 g of zirconium oxynitrate dihydrate and held at 40° C. and 24 l of a solution containing 886 g of ammonium bicarbonate and held at 40° C. were added to the above product at the same time with stirring, and they were further stirred for 30 minutes. The resulting insoluble precipitate was filtered and the filtrate was washed to form a slurry (slurry concentration 14% by weight). Then, in the same way as in Example 1, spray drying and calcining were carried out to afford a catalyst K having properties shown in Table 1.

COMPARATIVE EXAMPLE 4

A 5% ammonia aqueous solution was added dropwise to 10 l of an aqueous solution containing 288.2 g, calculated as silica, of sodium silicate (JIS No. 3), adjusted to pH of 2 with nitric acid and maintained at 40° C. Thus, pH of the aqueous solution was adjusted to 7.4 and an insoluble precipitate resulted. After the precipitate was filtered and the filtrate was washed, 15 l of deionized water was added to the cake containing 173.8 g of silica to provide a slurry.

Separately, a solution obtained by dissolving 317.4 g of copper nitrate trihydrate and 294.5 g of zinc nitrate hexahydrate in 5 l of deionized water and maintained at 40° C. was added to a solution of 400 g of ammonium bicarbonate in 20 l of deionized water, maintained at 40° C. to form an insoluble precipitate. Subsequently, the temperature was raised to 80° C. over the course of 40 minutes, and the product was aged for 30 minutes to form a catalyst precursor slurry. Next, the catalyst precursor slurry was mixed under stirring with the silica component-containing slurry prepared above, and the mixture was vigorously stirred for 30 minutes, followed by filtering and washing. The washed product was kneaded with a kneader to provide a slurry (slurry concentration 16% by weight). In the same as in Example 1, spray drying and calcining were carried out to afford a silica supported catalyst L having an average particle size of 63 μm.

TEST EXAMPLES 1–11 (ABRASION TEST)

Fifty grams each of the spherical catalyst powders (calcined products) obtained in Example 1–8 and Comparative Examples 1–3 was fluidized in a stream of nitrogen and maintained at 140° C. Subsequently, the nitrogen gas was gradually replaced with a hydrogen gas, and the whole amount of the nigrogen gas was replaced with the hydrogen gas over the course of 5 hours. The temperature was then maintained at 240° C. for 3 hours, and reduction of the catalyst was carried out.

Thereafter, a thick glass tube having an inner diameter of 270 mm and provided in a lower portion with small holes of 0.4 mmφ was filled with the above reduced catalyst, and a discharge tube having lest the catalyst powder was scattered out from the system a cylindrical filter paper was inserted in the upper portion of the glass tube.

Nitrogen was then jetted from the small holes in the lower portion for 1 hour at a rate of 510 l/hr to wear out the catalyst particles. Thereafter, jetting of nitrogen stopped, and the catalyst was reoxidized while air flowed little by little for 15 hours. Thus, almost the total amount of the powder was recovered.

Before or after the test, a particle size distribution of the catalyst particles was measured by a sonic-type hand shifter (SW-20 Model: a machine of Tsutsui Rikagakukiki K.K.), and an abrasion rate was found by the following equations.

$$AR(-20) = (A-B)/C \times 100 \ (\%)$$

$$AR(-44) = (D-E)/F \times 100 \ (\%)$$

AR(−20): Abrasion rate (%) found by change in a proportion of particles having a particle size of not more than 20 microns.

AR(−44): Abrasion rate (%) found by change in a proportion of particles having a particle size of not more than 44 microns.

A: Proportion (wt. %) of particles having a particle size of not more than 20 microns occupied in the catalyst particles (reoxidized product) recovered after the abrasion test.

B: Proportion (wt. %) of particles having a particle size of not more than 20 microns occupied in the catalyst particles before the abrasion test.

C: Proportion (wt. %) of particles having a particle size of not less than 20 microns occupied in the catalyst particles before the abrasion test.

D: Proportion (wt. %) of particles having a particle size of not more than 44 microns occupied in the catalyst particles (reoxidized product) recovered after the abrasion test.

E: Proportion (wt. %) of particles having a particle size of not more than 44 microns occupied in the catalyst particles before the abrasion test.

F: Proportion (wt. %) of particles having a particle size of not less than 44 microns occupied in the catalyst particles before the abrasion test.

The results obtained are shown in Table 1 together with the data of commercially available catalysts as Referential Examples. Test

TEST EXAMPLES 12-21 (ACTIVITY TEST)

One hundred milliliters each of the catalysts A-H, K and L was filled in a stainless steel reactor having an inner diameter of 30 mm and provided in a lower portion with a sintered metal filter. A nitrogen gas was introduced through the filter in the lower portion of the reactor, and the temperature was maintained at 140° C.

Subsequently, the nitrogen gas was gradually replaced with a hydrogen gas, and the whole amount of the nitrogen gas was replaced with the hydrogen gas over the course of about 5 hours. The temperature was then held at 240° C. for 3 hours, and reduction of the catalyst was carried out. Thereafter, the test for catalytic activity of the catalyst was run using a synthesis gas comprising 67.4% of hydrogen, 24.0% of carbon monoxide, 6.6% of carbon dioxide, 1.5% of methane, and 0.5% of nitrogen. The results are shown in Table 2.

TABLE 1

| | Catalyst | Zirconium oxide (based on oxide) (wt. %) | Atomic ratio at the time of preparing the catalyst | Apparent density of calcined product (g/ml) | Average particle size (μm) | Catalyst (calcined product) Particle size distribution (wt. %) | | | | | |
|---|---|---|---|---|---|---|---|---|---|---|---|
| | | | | | | μm −20 | +20 −44 | +44 −63 | +63 −88 | +88 −105 | +105 −149 | +149 |
| Test Example | | | | | | | | | | | | |
| 1 | A | 43 | Zr:Cu:Zn:Cr 1:1.11:0.83:0.07 | 1.04 | 61 | 0.4 | 17.0 | 38.3 | 25.3 | 12.8 | 6.0 | 0.2 |
| 2 | B | 47.2 | Zr:Cu:Zn:V 1:0.93:0.70:0.028 | 2.26 | 48 | 1.3 | 27.2 | 55.4 | 13.5 | 1.9 | 0.5 | 0.3 |
| 3 | C | 47.7 | Zr:Cu:Zn:Mg 1:0.93:0.7:0.1 | 1.11 | 56 | 1.3 | 18.5 | 50.1 | 22.6 | 5.6 | 1.8 | 0.1 |
| 4 | D | 47.9 | Zr:Cu:Zn:P 1:0.93:0.7:0.018 | 1.05 | 45 | 2.2 | 39.0 | 49.2 | 9.6 | 0.1> | 0.1> | 0.1> |
| 5 | E | 47.2 | Zr:Cu:Zn:Al 1:0.93:0.7:0.15 | 1.16 | 52 | 0.6 | 21.6 | 64.8 | 10.1 | 1.4 | 1.5 | 0.1 |
| 6 | F | 36.3 | Zr:Cu:Zn:Al 1:1.44:1.10:0.23 | 0.94 | 58 | 0.1 | 14.5 | 54.0 | 29.2 | 1.3 | 1.1 | 0.2 |
| 7 | G | 47.1 | Zr:Cu:Zn:Al 1:0.93:0.7:0.15 | 1.08 | 57 | 0.8 | 16.3 | 56.4 | 20.6 | 2.7 | 2.9 | 0.3 |
| 8 | H | 48.5 | Zr:Cu:Zn 1:0.93:0.7 | 1.10 | 59 | 0.1 | 20.0 | 43.3 | 33.0 | 1.5 | 2.1 | 0.1> |
| 9 | I | 0.0 | Zr:Cu:Zn:Al 0:1:0.75:0.16 | 0.82 | 47 | 1.2 | 34.4 | 53.6 | 7.0 | 2.2 | 1.3 | 1.4 |
| 10 | J | 28.5 | Zr:Cu:Zn:Al 1:2.0:1.5:0.54 | 0.98 | 55 | 0.9 | 16.8 | 57.4 | 18.1 | 5.3 | 1.3 | 0.2 |
| 11 | K | 73.5 | Zr:Cu:Zn:Al 1:0.3:0.226:0.045 | 1.21 | 50 | 0.66 | 31.0 | 65.0 | 2.9 | 0.48 | 0.37 | 0.17 |
| Referential Example | | | | | | | | | | | | |
| 1 | M*1 | — | Al2O3:SiO2 1:6.22 | 0.47 | 63 | 1.6 | 19.6 | 30.3 | 36.8 | 8.4 | 2.9 | 0.4 |
| 2 | N*2 | — | Al2O3:SiO2 1:2.28 | 0.43 | 64 | 4.4 | 20.5 | 23.6 | 29.8 | 13.0 | 7.5 | 1.2 |

| | Catalyst | Catalyst (after abrasion test, reoxidized product) | | | | | | | Abrasion rate (%) | |
|---|---|---|---|---|---|---|---|---|---|---|
| | | Average particle size (μm) | Particle size distribution (wt. %) | | | | | | AR (−20) | AR (−44) |
| | | | μm −20 | +20 −44 | +44 −63 | +63 −88 | +88 −105 | +105 −149 | +149 | | |
| Test Example | | | | | | | | | | | |
| 1 | A | 54 | 14.6 | 23.4 | 22.6 | 25.7 | 9.4 | 4.1 | 0.2 | 14.3 | 25.0 |
| 2 | B | 40 | 25.1 | 32.6 | 39.9 | 2.2 | 0.2 | 0.1 | 0.1> | 24.1 | 34.8 |
| 3 | C | 45 | 20.8 | 27.5 | 41.1 | 9.3 | 1.1 | 0.1 | 0.1> | 19.8 | 35.5 |
| 4 | D | 35 | 31.2 | 28.9 | 37.2 | 2.5 | 0.1> | 0.1> | 0.1> | 29.7 | 32.1 |
| 5 | E | 46 | 7.4 | 36.6 | 52.0 | 3.2 | 0.2 | 0.3 | 0.2 | 6.8 | 28.0 |

TABLE 1-continued

| | | | | | | | | | | |
|---|---|---|---|---|---|---|---|---|---|---|
| 6 | F | 47 | 28.1 | 20.8 | 32.5 | 18.3 | 0.1> | 0.1> | 0.1> | 28.0 | 40.2 |
| 7 | G | 48 | 9.2 | 30.1 | 51.0 | 8.1 | 1.0 | 0.4 | 0.2 | 8.5 | 26.8 |
| 8 | H | 49 | 8.0 | 30.4 | 41.0 | 20.4 | 0.1 | 0.1> | 0.1> | 7.9 | 22.9 |
| 9 | I | 19 | 50.8 | 31.1 | 15.8 | 2.0 | 0.1> | 0.1> | 0.1> | 50.2 | 71.9 |
| 10 | J | 28 | 41.6 | 23.6 | 33.8 | 0.5 | 0.5 | 0.1> | 0.1> | 41.1 | 57.7 |
| 11 | K | 45 | 13.87 | 32.24 | 53.83 | 0.06 | 0.1> | 0.1> | 0.1> | 13.3 | 21.1 |
| Referential Example | | | | | | | | | | | |
| 1 | M*1 | 48 | 21.8 | 24.9 | 23.9 | 22.6 | 5.1 | 1.4 | 0.2 | 20.6 | 32.4 |
| 2 | M*2 | 40 | 32.2 | 21.0 | 16.9 | 20.8 | 6.0 | 2.9 | 0.2 | 29.1 | 37.7 |

TABLE 2

| | Catalyst | Reaction pressure (kg/cm$^2$ · G) | SV (× 10$^4$ hr$^{-1}$) | Reaction temperature (°C.) | Concentration of methanol in reactor outlet gas (%) | CO conversion (%) | Space time yield of methanol (kg/l/hr) |
|---|---|---|---|---|---|---|---|
| Test Example | | | | | | | |
| 12 | A | 70 | 2.7 | 270 | 8.5 | 29.7 | 2.8 |
| 13 | B | 70 | 4.1 | 282 | 6.2 | 22.5 | 3.2 |
| 14 | C | 100 | 2.0 | 244 | 8.7 | 29.3 | 2.1 |
| 15 | D | 100 | 2.0 | 270 | 14.6 | 44.7 | 3.2 |
| 16 | E | 70 | 2.7 | 260 | 9.3 | 31.7 | 3.0 |
| 17 | F | 100 | 1.0 | 264 | 22.5 | 66.6 | 2.22 |
| 18 | G | 70 | 2.0 | 260 | 9.0 | 31.2 | 2.2 |
| 19 | H | 70 | 2.7 | 260 | 3.7 | 13.9 | 1.29 |
| 20 | K | 70 | 2.0 | 260 | 6.8 | 23.7 | 1.71 |
| 21 | L | 70 | 2.0 | 260 | 0.6 | 2.4 | 0.17 |

From the results of Tables 1 and 2, it follows that the process of this invention can provide the catalysts having the high catalytic activity and the abrasion resistance equal to the commercially available catalysts for gas-phase fluidized bed which are used in the other reaction.

What we claim is:

1. In a method for producing methanol by reacting carbon monoxide and/or carbon dioxide with hydrogen in a vapor phase in the presence of a fluidized catalyst, the improvement wherein the fluidized catalyst comprises a uniform mixture of copper oxide, zinc oxide, zirconium oxide and aluminum oxide, the content of copper oxide being 18 to 50% by weight, the content of zinc oxide being 10 to 20%, the content of zirconium oxide being 30 to 70% by weight and the content of aluminum oxide being 1 to 10% by weight based on the total weight of copper oxide and zinc oxide, and wherein said catalyst has a particle size of 20 to 400 microns and has been activated by reduction with a hydrogen-containing gas.

2. The method of claim 1 wherein the content of zirconium oxide is 40 to 60% by weight.

3. The method of claim 1 wherein the proportions of copper oxide and zinc oxide are such that the Cu/Zn atomic ratio is from 0.5/1 to 20.0/1.

4. The method of claim 1 wherein the Cu/Zn atomic ratio is from 0.8/1 to 15.0/1.

* * * * *